US009474728B2

(12) United States Patent
Lederman et al.

(10) Patent No.: US 9,474,728 B2
(45) Date of Patent: Oct. 25, 2016

(54) METHODS AND COMPOSITIONS FOR TREATING FATIGUE ASSOCIATED WITH DISORDERED SLEEP USING VERY LOW DOSE CYCLOBENZAPRINE

(71) Applicant: Tonix Pharma Holdings Limited, Hamilton (BM)

(72) Inventors: Seth Lederman, New York, NY (US); Herb Harris, Chapel Hill, NC (US)

(73) Assignee: Tonix Pharma Holdings Limited, Hamilton (BM)

( * ) Notice: Subject to any disclaimer, the term of this patent is extended or adjusted under 35 U.S.C. 154(b) by 0 days.

(21) Appl. No.: 14/477,981

(22) Filed: Sep. 5, 2014

(65) Prior Publication Data
US 2015/0065581 A1 Mar. 5, 2015

Related U.S. Application Data

(62) Division of application No. 13/157,270, filed on Jun. 9, 2011, now abandoned.

(60) Provisional application No. 61/358,305, filed on Jun. 24, 2010.

(51) Int. Cl.
*A61K 31/135* (2006.01)
*A61K 31/137* (2006.01)
*A61K 45/06* (2006.01)
*A61K 9/20* (2006.01)
*G06F 19/00* (2011.01)
*A61K 9/28* (2006.01)

(52) U.S. Cl.
CPC ........... *A61K 31/135* (2013.01); *A61K 9/2018* (2013.01); *A61K 9/2059* (2013.01); *A61K 31/137* (2013.01); *A61K 45/06* (2013.01); *G06F 19/70* (2013.01); *A61K 9/2866* (2013.01)

(58) Field of Classification Search
CPC .................................................. A61K 31/135
See application file for complete search history.

(56) References Cited

U.S. PATENT DOCUMENTS

| | | | |
|---|---|---|---|
| 4,968,507 A | 11/1990 | Zentner et al. |
| 5,073,543 A | 12/1991 | Marshall et al. |
| 5,120,548 A | 6/1992 | McClelland et al. |
| 5,439,686 A | 8/1995 | Desai et al. |
| 5,498,421 A | 3/1996 | Grinstaff et al. |
| 5,591,731 A | 1/1997 | Kennedy et al. |
| 5,591,767 A | 1/1997 | Mohr et al. |
| 5,639,476 A | 6/1997 | Oshlack et al. |
| 5,674,533 A | 10/1997 | Santus et al. |
| 5,733,566 A | 3/1998 | Lewis |
| 6,096,331 A | 8/2000 | Desai et al. |
| 6,248,363 B1 | 6/2001 | Patel et al. |
| 6,267,985 B1 | 7/2001 | Chen et al. |
| 6,309,663 B1 | 10/2001 | Patel et al. |
| 6,358,944 B1 | 3/2002 | Lederman et al. |
| 6,383,471 B1 | 5/2002 | Chen et al. |
| 6,395,788 B1 | 5/2002 | Iglehart |
| 6,506,405 B1 | 1/2003 | Desai et al. |
| 6,537,579 B1 | 3/2003 | Desai et al. |
| 6,541,523 B2 | 4/2003 | Iglehart |
| 6,720,001 B2 | 4/2004 | Chen et al. |
| 6,749,868 B1 | 6/2004 | Desai et al. |
| 6,753,006 B1 | 6/2004 | Desai et al. |
| 6,761,903 B2 | 7/2004 | Chen et al. |
| 7,105,486 B2 | 9/2006 | Mickle et al. |
| 7,223,735 B2 | 5/2007 | Mickle et al. |
| 7,532,935 B2 | 5/2009 | Maschino |
| 7,655,630 B2 | 2/2010 | Mickle et al. |
| 7,658,945 B2 | 2/2010 | Singh |
| 7,659,253 B2 | 2/2010 | Mickle et al. |
| 7,659,254 B2 | 2/2010 | Mickle et al. |
| 7,662,787 B2 | 2/2010 | Mickle et al. |
| 7,662,788 B2 | 2/2010 | Mickle et al. |
| 7,671,030 B2 | 3/2010 | Mickle et al. |
| 7,671,031 B2 | 3/2010 | Mickle et al. |
| 7,674,774 B2 | 3/2010 | Mickle et al. |
| 7,678,770 B2 | 3/2010 | Mickle et al. |
| 7,678,771 B2 | 3/2010 | Mickle et al. |
| 7,682,628 B2 | 3/2010 | Singh |
| 7,687,466 B2 | 3/2010 | Mickle et al. |
| 7,687,467 B2 | 3/2010 | Mickle et al. |
| 7,700,561 B2 | 4/2010 | Mickle et al. |
| 7,713,936 B2 | 5/2010 | Mickle et al. |
| 7,718,619 B2 | 5/2010 | Mickle et al. |
| 7,723,305 B2 | 5/2010 | Mickle et al. |

(Continued)

FOREIGN PATENT DOCUMENTS

WO WO-9918937 4/1999
WO WO-9958115 11/1999

(Continued)

OTHER PUBLICATIONS

Aaronson et al., "Defining and measuring fatigue," Image J. Nurs. Sch., 31:45-50 (1999).
Abd el-Fattah et al., "Enhancement of dissolution rate of hydrochlorothiazide via solid dispersion," Pharmazie., 41:790-793 (1986).
Abernethly et al., "Absolute bioavailability of imipramine: influence of food," Psychoharmacology (Berl.), 83:104-106 (1984).
Adler et al., "Randomized trial of modafinil for treating subjective daytime sleepiness in patients with Parkinson's disease," Movement Disorders : Official Journal of the Movement Disorder Society, 18(3), 287-293 (2003).
Amin et al., "Indion 414 as superdisintegrant in formulation of mouth dissolve tablets," Indian Journal of Pharmaceutical Sciences, 68:117-119 (2006).

(Continued)

*Primary Examiner* — Samira Jean-Louis
(74) *Attorney, Agent, or Firm* — Ropes & Gray LLP

(57) ABSTRACT

The present invention relates to methods for the treatment or prevention of fatigue associated with disordered sleep, for example, in multiple sclerosis, fibromyalgia, Fabry's disease, Parkinson's disease, or traumatic brain injury, using cyclobenzaprine. The present invention further relates to a biomarker for the therapeutic effects of a cyclobenzaprine treatment.

2 Claims, No Drawings

(56) References Cited

U.S. PATENT DOCUMENTS

| | | | |
|---|---|---|---|
| RE41,884 | E | 10/2010 | Garavilla et al. |
| 7,820,788 | B2 | 10/2010 | Desai et al. |
| 7,923,536 | B2 | 4/2011 | Desai et al. |
| 8,093,300 | B2 | 1/2012 | Lederman |
| 8,138,229 | B2 | 3/2012 | Desai et al. |
| 2003/0077227 | A1 | 4/2003 | Dugger |
| 2003/0077297 | A1 | 4/2003 | Chen et al. |
| 2005/0096327 | A1 | 5/2005 | Caprathe et al. |
| 2005/0181041 | A1 | 8/2005 | Goldman |
| 2006/0073189 | A1 | 4/2006 | Pinney et al. |
| 2007/0141144 | A1 | 6/2007 | Roberts et al. |
| 2008/0146672 | A1 | 6/2008 | Denton et al. |
| 2009/0054403 | A1 | 2/2009 | Woiwode et al. |
| 2009/0098200 | A1 | 4/2009 | Krayz et al. |
| 2009/0275541 | A1 | 11/2009 | Sullivan |
| 2010/0021507 | A1 | 1/2010 | Bunick et al. |
| 2010/0098832 | A1 | 4/2010 | Venkatesh et al. |
| 2010/0247649 | A1 | 9/2010 | Palaparthi et al. |
| 2010/0266682 | A1 | 10/2010 | Davar et al. |
| 2011/0068511 | A1 | 3/2011 | Sowden et al. |
| 2011/0124656 | A1 | 5/2011 | Seth et al. |
| 2011/0319389 | A1 | 12/2011 | Lederman et al. |
| 2012/0101154 | A1 | 4/2012 | Lederman et al. |
| 2012/0232159 | A1 | 9/2012 | Lederman |
| 2013/0165511 | A1 | 6/2013 | Lederman et al. |
| 2014/0171515 | A1 | 6/2014 | Lederman |
| 2014/0336264 | A1 | 11/2014 | Nebuloni |
| 2016/0030576 | A1 | 2/2016 | Newbuloni |

FOREIGN PATENT DOCUMENTS

| | | |
|---|---|---|
| WO | WO-0112174 | 2/2001 |
| WO | WO-0112175 | 2/2001 |
| WO | WO-0189476 | 11/2001 |
| WO | WO-2004039320 | 5/2004 |
| WO | WO-2005051297 | 6/2005 |
| WO | WO-2007038620 | 4/2007 |
| WO | WO-2009002770 | 12/2008 |
| WO | WO-2009089494 | 7/2009 |
| WO | WO-2011062614 | 5/2011 |
| WO | WO-2014145156 | 9/2014 |

OTHER PUBLICATIONS

Amitai et al., "Distribution of amitriptyline and nortriptyline in blood: role of alpha-1-glycoprotein," Ther. Drug Monit., 15:267-273 (1993).

Arnold et al., "Antidepressant treatment of fibromyalgia. A meta-analysis and review," Psychosomatics, 41:104-113 (2000).

Bagul, "Current status of table disintegrants: a review," retrieved from [http://www.pharmainfo.net/reviews/current-status-tablet-disintegrantsa-review] (2006) 13 pages.

Balant et al., "Prodrugs for the improvement of drug absorption via different routes of administration," Eur. J. Drug Metab. Pharmacokinet., 15:143-153 (1990).

Balasubramaniam et al., "Effects of superdisintegrants on dissolution of cationic drugs," Dissolution Technologies, 18-25 (2008).

Barker et al., "Identification of a single amino acid, phenylalanine 586, that is responsible for high affinity interactions of tricyclic antidepressants with the human serotonin transporter," Mol. Pharmacol., 50:957-965 (1996).

Barnes et al., "Brainstem noradrenergic system depression by cyclobenzaprine," Neuropharmacology, 19:221-224 (1980).

Bartoli et al., "An atypical case of reverse Takotsubo cardiomyopathy during general anesthesia in a 30-year-old male with post-traumatic stress disorder," J. Cardiothorac Vasc. Anesth., 25:1116-1118 (2011).

Baumann et al., "Amitriptyline pharmacokinetics and clinical response: I. Free and total plasma amitriptyline and nortriptylanine," Int. Clin. Psychopharmacol., 1:89-101 (1986).

Bennett et al., "A comparision of cyclobenzaprine and placebo in the management of fibrositis: A double-blind controlled study," Arthiritis Rheum., 31:1535-1542 (1988).

Berezhkovskiy et al., "Prediction of the possibility of the second peak of drug plasma concentration time curve after iv bolus administration from the standpoint of the traditional multi-compartmental linear pharmacokinetics," J. Pharm. Sci., 97:2385-2393 (2008).

Bhatt et al., "Development and validation of amitriptyline and its metabolite in human plasma by ultra performance liquid chromatography—tandem mass spectrometry and its application to a bioequivalence study," Biomedical Chromatography, 24:1247-1254 (2010).

Bhowmik et al., "Fast dissolving tablet: an overview," Journal of Chemical and Pharmaceutical Research, 1:163-177 (2009).

Bi et al., "Mechanism of eutectic formation upon compaction and its effects on tablet properties," Thermochimica Acta, 404:213-226 (2003).

Bickel et al., "Buccal absorption and other properties of pharmacokinetic importance of imipramine and its metabolites," J. Pharm Pharmacol., 21:160-168 (1969).

Blake et al.,"The development of a clinician-administered PTSD scale," Journal of Traumatic Stress, 8:75-90 (1995).

Braithwaite et al., "Plasma concentration of amitriptyline and clinical response," Lancet., 17:1297-1300 (1972).

Breyer-Pfaff et al., "Comparative N-glucuronidation kinetics of ketotifen and amitriptyline by expressed human UDP-glucuronosyltransferases and liver microsomes," Drug Metab. Dispos., 28:869-872 (2000).

Brittain, "A summary of the scholarly activities associated with Center for Pharmaceutical Physics," Journal of Pharmaceutical Physics, vol. 11 (2009) 24 pages.

Brittain, "Profiles of Drug Substances, Excipients, and Related Methodology," Journal of Pharmaceutical Physics, vol. 12 (2010) 14 pages.

Bundgaard, "Novel chemical approaches in prodrug design," Drugs of the Future, 16:443-458 (1991).

Cai et al., "A humanized UGT1 mouse model expressing the UGT1A1*28 allele for assessing drug clearance by UGT1A1-dependent glucuronidation," Drug Metab. Dispos., 38:879-886 (2010).

Caillé et al., "Pharmacokinetics of two lorazepam formulations, oral and sublingual, after multiple doses," Biopharmaceutics and Drug Disposition, 4(1):31-42 (1983).

Campbell-Roberts et al., "Quantitative analysis of mannitol polymorphs. X-ray powder diffractometry—exploring preferred orientation effects," J. Pharm. Biomed. Anal., 28:1149-1159 (2002).

Cantini et al., "[Fluoxetin combined with cyclobenzaprine in the treatment of fibromyalgia]," Minerva Med., 85:97-100 (1994) Abstract in English.

Cavaljuga et al., "Therapeutic effects of two antidepressant agents in the treatment of posttraumatic stress disorder (PTSD)," Bosn J. Basic Med. Sci., 3:12-16 (2003).

Commissiong et al., "Cyclobenzaprine: a possible mechanism of action for its muscle relaxant effect," Can. J. Physicol. Pharmacol., 59:37-44 (1981).

Cotton et al., "Cyclobenzaprine hydrochloride," Anal Profiles Drug Subs, 17:41-72 (1988).

Cyclobenzaprine (Flexeril),eMedExpert.com—Facts, Oct. 5, 2008, pp. 1-2, XP055239326,Retrieved from the Internet: URL:http://www.emedexpert.com/facts/cyclobenzaprine-facts.shtml [retrieved on Jan. 7, 2016].

Davies et al., "Multiple peaking phenomena in pharmacokinetic disposition," Clinical Pharmacokinetics, 49:351-377 (2010).

Descamps et al., "Transformation of pharmaceutical compounds upon milling and comilling: the role of T(g)," J. Pharm. Sci., 96:1398-1407 (2007).

Dobrinska, "Enterohepatic circulation of drugs," J. Clin. Pharmacol., 29:577-580 (1989).

El-Banna et al., "Physicochemical study of drug binary systems. Part 3: Tolbutamide-urea and tolbutamide-mannitol systems," Pharmazie , 30:788-792 (1975).

El-Banna et al., "The application of solid dispersion technique in the preparation of therapeutic tablets. Part 1: Paracetamol, amylobarbitone, and caffeine tablets," Pharmazie, 32:511-515 (1977).

(56) References Cited

OTHER PUBLICATIONS

Ereshefsky et al., "Pharmacokinetic factors affecting antidepressant drug clearance and clinical effect: evaluation of doxepin and imipramine—new data and review," Clin. Chem., 34:863-880 (1988).
FDA guidance for industry, bioavailability and bioequivalence studies for orally administered drug products—general considerations, US Dept. of Health and Human Services, FDA, Center for Drug Evaluation and Research (2003) 26 pages.
Fibromyalgia: medications for fibromyalgia. Jun. 12, 2008 (3 pages) Tricyclic anti-depressants Citation is not enclosed due to copyright restrictions. A copy may be obtained from the Wayback Machine at https://web.archive.org/web/20080612014615/http://www.spinehealth.com/conditions/fibromyalgia/fibromyalgia-medications-fibromyalgia.
Fossaluzza et al., "Combined therapy with cyclobenzaprine and ibuprofen in primary fibromyalgia syndrome," Int. J. Clin. Pharmacol. Res., 12:99-102 (1992).
Fronczek et al., "Three polymorphs (alpha, beta, and delta) of D-mannitol at 100 K," Acta Crystallographica Section C, 59:o567-o570 (2003).
Fujiwara et al., "Developmental hyperbilirubinemia and CNS toxicity in mice humanized with the UDP glucuronosyltransferase 1 (UGT1) locus," Proc. Natl. Acad. Sci., USA, 107:5024-5029 (2010).
Gai et al., "Bioavailability of a controlled-release cyclobenzaprine tablet and influence of a high fat meal on bioavailability," Int. J. Clin. Pharmacol. Ther., 47:269-274 (2009).
Godfrey, "A guide to the understanding and use of tricyclic antidepressants in the overall management of fibromyalgia and other chronic pain syndromes," Arch. Intern. Med., 156:1047-1052 (1996).
Green et al., "Glucuronidation of amine substrates by purified and expressed UDP-glucuronosyltransferase proteins," Drug Metab. Dispos., 26:860-867 (1998).
Grof et al., "Preliminary comparative trial of proheptatriene and imipramine in the treatment of depressions (An intensive and controlled study)," Activitas Nervosa Superior, 7:288-289 (1965).
Guo et al., "Liquid chromatography-tandem mass spectrometry method for measurement of nicotine N-glucuronide: a marker for human UGT2B10 inhibition," J. Pharm. Biomed. Anal., 55:964-971 (2011).
Halvani et al., "The relation between shift work, sleepiness, fatigue and accidents in Iranian Industrial Mining Group workers," Industrial Health, 47(2), 134-138 (2009).
Havlikova et al., "Fatigue in Parkinson's disease is not related to excessive sleepiness or quality of sleep," Journal of the Neurological Sciences, 270(1-2), 107-113 (2008).
Hawes, "N+-glucuronidation, a common pathway in human metabolism of drugs with a tertiary amine group," Drug Metab. Dispos., 26:830-837 (1998).
Hiller et al., "Retigabine N-glucuronidation and its potential role in enterohepatic circulation," Drug Metab. Dispos., 27:605-612 (1999).
Honda et al., "Tricyclic analogs cyclobenzaprine, amitriptyline and cyproheptadine inhibit the spinal reflex transmission through 5-HT(2) receptors," Eur. J. Pharmacol., 458:91-99 (2003).
Hucker et al., "Metabolism of cyclobenzaprine in the dog," Drug Metab. Dispos., 6:184-192 (1978).
Hucker et al., "Physiological disposition and metabolism of cyclobenzaprine in the rat, dog, rhesus monkey, and man," Drug Metab. Dispos., 6:659-672 (1978).
Hucker et al., "Plasma levels and bioavailability of cyclobenzaprine in human subjects," J. Clin. Pharmacol., 17:719-727 (1977).
Jorgensen et al., "Pharmacokinetics of amitriptyline infused intravenously in man," Eur. J. Clin. Pharmacol., 10:337-341 (1976).
Kaivosaari et al., "N-glucuronidation of drugs and other xenobiotics by human and animal UDP-glucuronosyltransferases," Xenobiotica., 41:652-669 (2011).
Katz et al., "Cyclobenzaprine in the treatment of acute muscle spasm: review of a decade of clinical experience," Clinical Therapeutics, 10:216-228 (1988).
Kobayashi et al., "Cyclobenzaprine, a centrally acting muscle relaxant, acts on descending serotonergic systems," Eur. J. Pharmacol., 311:29-35 (1996).
Kornhuber et al., "Identification of new functional inhibitors of acid sphingomyelinase using a structure-property-activity relation model," J. Med. Chem., 51:219-237 (2008).
Krishnan et al., "The molecular neurobiology of depression," Nature, 455:894-902 (2008).
Kubo et al., "Improvement of dissolution rate and oral bioavailability of a sparingly water-soluble drug, (+/−)-5- [[2-(2-naphthalenylmethyl)-5-benzoxazoly1]-methyl]-2,4-thiazolidinedione, in co-ground mixture with D-mannitol," Biol. Pharm. Bull., 20:460-463 (1997).
Lee et al., "Transinactivation of the epidermal growth factor receptor tyrosine kinase and focal adhesion kinase phosphorylation by dietary flavonoids: effect on invasive potential of human carcinoma cells," Biochem. Pharmacol., 67:2103-0114 (2004).
Link et al., "Cardiovascular regulation in mice lacking alpha2-adrenergic receptor subtypes b and c," Science, 273:803-805 (1996).
Lower et al., "Armodafinil for sarcoidosis-associated fatigue: a double-blind, placebo-controlled, crossover trial." Journal of Pain and Symptom Management, 45(2), 159-169 (2013).
Miles et al., "An investigation of human and rat liver microsomal mycophenolic acid glucuronidation: evidence for a principal role of UGT1A enzymes and species differences in UGT1A specificity," Drug Metab. Dispos., 33:1513-1520 (2005).
Moldofsky et al., "Effects of bedtime very low dose cyclobenzaprine on symptoms and sleep physiology in patients with fibromyalgia syndrome: a double-blind randomized placebo-controlled study," J. Rheum., 38:2653-2663 (2011).
Narang et al., "Sublingual mucosa as a route for systemic drug delivery," Int. J. Pharma., Sci., 3:18-22 (2011).
Nelson, "Experimental Determination of 2-component Phase Diagrams," retrieved from http://www.tulane.edu/-sanelson/eens211/2compphasdiag.html, Feb. 7, 2011, 12 pages.
Ohshima et al., "Tissue distribution and metabolism of amitriptyline after repeated administration in rats," Drug Metab. Dispos., 22:21-25 (1994).
Overo et al., "Kinetics of nortriptyline in man according to a two compartment model," Eur. J. Clin. Pharmacol., 8:343-347 (1975).
Price et al., "Single-dose pharmacokinetics of sublingual versus oral administration of micronized 17 beta-estradiol," Obstetrics and Gynecology, 89(3):340-345 (1997).
Protocol Registration Receipt Jun. 26, 2012, "Comparative bioavailability of sublingual TNX-102, oral and intravenous cyclobenzaprine in healthy adults" 4 pages.
Razaghi et al., "Investigation of cyclobenzaprine hydrochloride release from oral osmotic delivery systems containing a water-swellable polymer," Drug Dev. Ind. Pharma., 28:631-639 (2002).
Rizzi et al.,"Cyclic alternating pattern: a new marker of sleep alteration in patients with fibromyalgia?," J. Rheumatol., 31:1193-1199 (2004).
Rosa et al.,"Automatic detection of cyclic alternating pattern (CAP) sequences in sleep: preliminary results," Clinical Neurophysiology, 110:585-592 (1999).
RX-s.net Retrieved from the Internet: URL:https://web.archive.org/web/20060516153148/http:l/rx-s.net/weblog/more/cyclobenzaprine_flexerilreg/ [retrieved on Mar. 12, 2013], from 2006 (2 pages).
Santandrea et al., "A double-blind crossover study of two cyclobenzaprine regimens in primary fibromyalgia syndrome," J. Int. Med. Res., 21:74-80 (1993).
Shen et al., "Distinguishing sleepiness and fatigue: focus on definition and measurement," Sleep Medicine Review, 10:63-76 (2006).
Sheng et al. "Efficacy of Modafinil on Fatigue and Excessive Daytime Sleepiness Associated with Neurological Disorders: A Systematic Review and Meta-Analysis," PLoS One, 8(12), e81802 (2013).

(56) References Cited

OTHER PUBLICATIONS

Shukla et al., "Mouth dissolving tablets I: an overview of formulation," Technology Scientia Pharmaceutica, 76:309-326 (2009).
Siddegowda et al., "Cyclo¬benzaprinium chloride," Acta Crystallogr. Sect. E Struct. Rep. Online. Jul. 1, 2011; 67(Pt 7): o1846 (Abstract only) 2 pages.
Singh et al., "Tablet disintegrants: an Overview," American Journal of Pharmtech Research (2012) 10 pages.
Stankoff et al., Modafinil for fatigue in MS: a randomized placebo-controlled double-blind study. Neurology, 64(7), 1139-1143 (2005).
Sutfin et al., "The analysis and disposition of imipramine and its active metabolites in man," Psychopharmacology (Berl.), 82:310-317 (1984).
Telang et al., "Crystallization of D-mannitol in binary mixtures with NaCl: phase diagram and polymorphism," Pharm. Res., 20:1939-1945 (2003).
Terzano et al., "Atlas, rules, and recording techniques for the scoring of cyclic alternating pattern sleep," Sleep Med., 3:187-199 (2002).
Terzano et al., "Polysomnographic analysis of arousal responses in obstructive sleep apnea syndrome by means of the cyclic alternating pattern," J. Clin. Neurophysiol., 13:145-155 (1996).
Thomas et al., "Sleep as a window into the world of fibromyalgia syndrome," J. Rheumatol., 38:2499-2500 (2011).
Tieleman et al., "Poor sleep quality and fatigue but no excessive daytime sleepiness in myotonic dystrophy type 2," Journal of Neurology, Neurosurgery, and Psychiatry, 81(9), 963-967 (2010).
Till et al., "Evidence for route dependent biotransformation of cyclobenzaprine hydrochloride," Biopharm. Drug Dispos., 3:19-28 (1982).
Tukey et al., "Human UDP-glucuronosyltransferases: metabolism, expression, and disease," Annu. Rev. Pharmacol. Toxicol., 40:581-616 (2000).
Vaddady et al., "In vitro pharmacokinetic/pharmacodynamic models in anti-infective drug development: focus on TB," Future Med. Chem., 2:1355-1369 (2010).
Vinar et al., "Proheptatriene in depression (extensive study)," Activitas Nervosa Superior, 7:290 (1965).
Wang et al., "Identification of human liver cytochrome P450 isoforms involved in the in vitro metabolism of cyclobenzaprine," Drug Metab. Dispos. 24:786-791 (1996).
Way et al., "Isotope dilution gas chromatographic-mass spectrometric measurement of tricyclic antidepressant drugs. Utility of the 4-carbethoxyhexafluorobutyryl derivatives of secondary amines," J. Anal Toxicol., 22:374-382 (1998).
Weaver et al., "An instrument to measure functional status outcomes for disorders of excessive sleepiness," Sleep, 20(10):835-843 (1997).
Winchell et al., "Cyclobenzaprine pharmacokinetics, including the effects of age, gender, and hepatic insufficiency," J. Clinical Pharmacol., 42:61-69 (2002).
Wong et al., "Potential interference of cyclobenzaprine and norcyclobenzaprine with HPLC measurement of amitriptyline and nortriptyline: resolution by GC-MS analysis," J. Anal Toxicol., 19:218-224 (1995).
Yan et al., "Absolute bioavailability and stereoselective pharmacokinetics of doxepin," Xenobiotica., 32:615-623 (2002).
Zajc et al., "Physical properties and dissolution behaviour of nifedipine/mannitol solid dispersions prepared by hot melt method," Int. J. Pharm., 291:51-58 (2004).
Zelapar Full Prescribing Information, Cardinal Health, Inc., Valeant Pharmaceuticals North America, Jul. 2006 2 pages.
Zhang et al., "Concepts and challenges in quantitative pharmacology and model-based drug development," AAPS J., 10:552-559 (2008).
Zhou et al., "Role of human UGT2B10 in N-glucuronidation of tricyclic antidepressants, amitriptyline, imipramine, clomipramine, and trimipramine," Drug Metab. Dispos., 38:863-870 (2010).

METHODS AND COMPOSITIONS FOR TREATING FATIGUE ASSOCIATED WITH DISORDERED SLEEP USING VERY LOW DOSE CYCLOBENZAPRINE

CROSS-REFERENCE TO RELATED APPLICATIONS

This application is a divisional application of U.S. patent application Ser. No. 13/157,270, filed Jun. 9, 2011, which claims priority from U.S. Provisional Application No. 61/358,305, filed Jun. 24, 2010. The contents of the foregoing priority applications are incorporated by reference herein in their entirety.

FIELD OF THE INVENTION

The present invention relates to methods for the treatment or prevention of fatigue associated with disordered sleep, for example, in multiple sclerosis, Fabry's disease, fibromyalgia, Parkinson's disease, or traumatic brain injury using cyclobenzaprine. The present invention further relates to a biomarker for assessing treatment effects on disordered sleep using cyclobenzaprine.

BACKGROUND OF THE INVENTION

Cyclobenzaprine, or 3-(5H-dibenzo[a,d]cyclohepten-5-ylidene)-N,N-dimethyl-1-propanamine, was first approved by the U.S. Food and Drug Administration in 1977 for the treatment of acute muscle spasms of local origin. (Katz, W., et al., *Cyclobenzaprine in the Treatment of Acute Muscle Spasm: Review of a Decade of Clinical Experience*, Clinical Therapeutics 10:216-228 (1988)). Cyclobenzaprine has also been studied in the treatment of fibromyalgia. In a study of 120 fibromyalgia patients, those receiving cyclobenzaprine (10 to 40 mg) over a 12-week period had significantly improved quality of sleep and pain score. There was also a reduction in the total number of tender points and muscle tightness (Bennett R M, et al. *A Comparison of Cyclobenzaprine and Placebo in the Management of Fibrositis: A Double-Blind Controlled Study*, Arthiritis Rheum. 1988; 31(12):1535-42).

Furthermore, the utility of a very low dose cyclobenzaprine as an agent for improving the quality of sleep, as a sleep deepener, or for treating sleep disturbances has been investigated. The very low dosage regimen was viewed as particularly useful in treating sleep disturbances caused by, exacerbated by or associated with fibromyalgia syndrome, prolonged fatigue, chronic fatigue, chronic fatigue syndrome, a sleep disorder, a psychogenic pain disorder, chronic pain syndrome (type II), the administration of a drug, autoimmune disease, stress or anxiety or for treating an illness caused by or exacerbated by sleep disturbances, and symptoms of such illness and generalized anxiety disorder. See U.S. Pat. Nos. 6,395,788 and 6,358,944, herein incorporated by reference.

It is important to develop new methods and pharmaceutical compositions that ameliorate fatigue associated with disordered sleep to improve symptoms found in fibromyalgia, multiple sclerosis, Fabry's disease, traumatic brain injury or Parkinson's disease.

SUMMARY OF THE INVENTION

In one aspect the invention is a method for treating or preventing fatigue associated with a sleep disorder associated with fibromyalgia, multiple sclerosis, Fabry's disease, traumatic brain injury or Parkinson's disease. The method comprises administering to a human in need of such treatment a pharmaceutical composition comprising cyclobenzaprine in a therapeutically effective amount and a therapeutically effective carrier, wherein such treatment ameliorates or eliminates the symptoms. The cyclobenzaprine may be administered at a dose between 0.1 mg to 50 mg/day. In one embodiment the cyclobenzaprine is administered at a low dose of less than 5 mg/day, such 1 mg/day or 2.5 mg/day. In another embodiment, the cyclobenzaprine may be administered at doses between 5 mg and 12 mg/day, such as 7 mg/day or 10 mg/day.

The method may further entail administering sequentially or concurrently a drug selected from the group consisting of an alpha-1-adrenergic receptor antagonist, a beta-adrenergic antagonist, an anticonvulsant, a selective serotonin reuptake inhibitor or a serotonin-norepinephrine reuptake inhibitor. Exemplary drugs include prazosin, sertraline, paroxetine, fluoxetine, citalopram and escitalopram.

In another aspect, the invention is a method for relieving muscle spasticity encountered in multiple sclerosis or Parkinson's disease. The method comprises administering cyclobenzaprine to relieve the spasticity. The cyclobenzaprine may be administered at a dose between 0.1 mg to 50 mg/day. In one embodiment, cyclobenzaprine is administered at a low dose of less than 5 mg/day, such 1 mg/day, or 2.5 mg/day. In another embodiment, the cyclobenzaprine may be administered at doses higher between 5 mg and 12 mg/day, such as 7 mg/day or 10 mg/day.

In yet another aspect, the invention is a biomarker or method for monitoring the effectiveness of a cyclobenzaprine treatment for disordered sleep. The method comprises determining CAP A1, A2 and A3 rates, and calculating an nCAP A2+A3 (or $CAP_{A2+A3(Norm)}$) value to determine whether a specified $CAP_{A2+A3(Norm)}$ threshold is achieved. When the specified $CAP_{A2+A3(Norm)}$ threshold is achieved the cyclobenzaprine treatment is considered effective. Typically the threshold is $CAP_{A2+A3(Norm)} \leq 33\%$, such 10%, 15%, 20%, 25%, 30% or 33%.

DETAILED DESCRIPTION OF THE INVENTION

In one aspect the invention is a method for treating fatigue associated with disordered sleep in conditions characterized by chronic fatigue including multiple sclerosis, fibromyalgia, Parkinson's disease, Fabry's disease, or traumatic brain injury. We have shown that improvement in fatigue is strongly associated with normalization of disordered sleep and that cyclobenzaprine normalizes disordered sleep. This normalization of sleep is measured by cyclic alternating pattern (CAP) analysis. Fatigue and disordered sleep may be symptoms of diseases including fibromyalgia, traumatic brain injury, Parkinson's disease, Fabry's disease, or multiple sclerosis. Traumatic brain injury and multiple sclerosis have muscle spasticity components that cyclobenzaprine can target along with disordered sleep and fatigue.

Furthermore, we have identified a biomarker for investigating the effectiveness of cyclobenzaprine treatment for fatigue associated with disordered sleep. Specifically, we have identified $CAP_{A2+A3(Norm)} \leq 33\%$ as a threshold for effectiveness for cyclobenzaprine treatment. The method entails measuring $CAP_{A1}$, $CAP_{A2}$ and $CAP_{A2}$ at different times or doses during treatment. $CAP_{A2+A3(Norm)}$ is then determined to identify whether a cyclobenzaprine treatment course is effective.

Fatigue may be defined as: "The awareness of a decreased capacity for physical and/or mental activity due to an imbalance in the availability, utilization, and/or restoration of resources needed to perform activity" (Aaronson, et al. (1999), *Defining and measuring fatigue*. Image J Nurs Sch 31(1): 45-50). Fatigue is commonly measured by rating scales such as the Fatigue Impact Scale.

CAP is a sleep EEC measurement consisting of transient arousals (phase A) that periodically interrupt the tonic theta/delta activities of NREM sleep (phase B) (Terzano, Parrino et al. (1996). *Polysomnographic analysis of arousal responses in obstructive sleep apnea syndrome by means of the cyclic alternating pattern* J Clin Neurophysiol 13(2): 145-55). Functionally, CAP translates a condition of sustained arousal instability oscillating between a greater arousal level (phase A) and a lesser arousal level (phase B). Arousal can be considered as a short transient intrusion of wakefulness EEC rhythms into sleep. An increased level of arousability might be related to sleep fragmentation. CAP is a spontaneous rhythm detectable during NREM sleep in form of EEG amplitude oscillations composed of an EEC transient pattern (phase A of the cycle) separated by intervals of background activity (phase B of the cycle). Three main EEC patterns have been described according to the prevalence of EEC synchrony (subtype A1, or $CAP_{A1}$), prevalence of EEC desynchrony (subtype A3, or $CAP_{A3}$), or a combination of both (subtype A2, or $CAP_{A2}$) (Terzano, Parrino et al. (2001, 2002). *Atlas, rules, and recording techniques for the scoring of cyclic alternating pattern* Sleep Med., 2(6) 537-553 and 3(2) 187-199).

"Cyclobenzaprine" includes cyclobenzaprine or a metabolite thereof, prodrug of cyclobenzaprine, a metabolite thereof, or a compound related to cyclobenzaprine. Metabolites of cyclobenzaprine useful according to the methods of this invention are metabolites that have substantially the same activity or better as cyclobenzaprine in alleviating symptoms. Cyclobenzaprine metabolites that may be useful according to this invention include CBP 10,11-trans-dihydriol, N-desmethyl-2-hydroxycyclobenzaprine, 3-hydroxycyclobenzaprine, N-desmethylcyclobezaprine, cyclobenzaprine N-oxide or a chiral isomer of these metabolites. A prodrug of cyclobenzaprine is a derivative of cyclobenzaprine that is metabolized in vivo into the active agent. Prodrugs useful according to this invention are those that have substantially the same activity or better than cyclobenzaprine in treating or preventing the symptoms of fibromyalgia, multiple sclerosis, Fabry's disease, traumatic brain injury or Parkinson's disease. Methods for making prodrugs are readily known in the art (e.g., Balant, L. P., *Prodrugs for the Improvement of Drug Absorption Via Different Routes of Administration*, Eur. J. Drug Metab. Pharmacokinet. 15:143-153 (1990); and Bundgaard, H., *Novel Chemical Approaches in Prodrug Design, Drugs of the Future* 16:443-458 (1991); incorporated by reference herein). A compound related to cyclobenzaprine is a compound with substantially the same activity as cyclobenzaprine, such as amitryptyline nortriptyline.

As used herein, a "therapeutically effective amount" of cyclobenzaprine for the purposes of this invention refers to the amount of the compound that prevents or alleviates or eliminates or interferes with disordered sleep. A physician can readily determine when symptoms are prevented or alleviated or eliminated, for example through clinical observation of a subject, or through reporting of symptoms by the subject during the course of treatment. One skilled in the art can readily determine an effective amount of a cyclobenzaprine to be administered, by taking into account factors such as the size, weight, age and sex of the subject, the extent of disease penetration or persistence and severity of symptoms, and the route of administration. Generally, a therapeutically effective amount of cyclobenzaprine administered to a subject is between 0.1 mg to about 50 mg/day, between 0.5 to about 12 mg/day, between 1 mg and 12 mg/day, or between 1 and 4 mg/day. Higher or lower doses are also contemplated.

In one embodiment the cyclobenzaprine is administered at a very low dose to minimize side effects observed at higher doses. The low doses include doses of less than 5 mg/day or less than 2.5 mg/day. Even lower doses are also contemplated. Generally, cyclobenzaprine therapy can be carried out indefinitely to alleviate the symptoms of interest and frequency of dosage may be changed to be taken as needed. The period of treatment should be carried out for as long as necessary to alleviate one or more of fibromyalgia, multiple sclerosis, Fabry's disease, traumatic brain injury or Parkinson's disease symptoms and the cyclobenzaprine administered at night-time and at an appropriate dose.

In another embodiment of the invention, cyclobenzaprine is administered in combination with a drug which may further alleviate the symptoms of fatigue. The drugs may be administered sequentially or concurrently with the cyclobenzaprine. The drugs include an alpha-1-adrenergic receptor antagonist, a beta-adrenergic antagonist, an anticonvulsant, a selective serotonin reuptake inhibitor or a serotonin-norepinephrine reuptake inhibitor, Exemplary selective serotonin reuptake inhibitor or a serotonin norepinephrine reuptake inhibitor include, but are not limited to, buproprion (at a dose between about 105 mg and 450 mg/day), citalopram (at a dose between about 10 mg and 40 mg/day), desvenlafaxine (at a dose between about 50 mg and 400 mg/day), duloxetine (at a dose between about 40 mg and 120 mg/day), escitalopram (at a dose between about 10 mg and 20 mg/day), fluoxetine (at a dose between about 20 mg and 80 mg/day), fluvoxamine (at a dose between about 100 mg and 300 mg/day), milnacipran (at a dose between about 30 mg and 200 mg/day), paroxetine (at a dose between about 20 mg and 50 mg/day), sertraline (at a dose between about 50 mg and 200 mg/day), tradodone (at a dose between about 150 mg and 600 mg/day), and venlafaxine (at a dose between about 75 mg and 225 mg/day). Exemplary anticonvulsants include, but are not limited to carbamazepine (at a dose between about 400 mg and 1200 mg/day), gabapentin (at a dose between about 900-1800 mg/day), lamotrigine (at a dose between about 100 mg and 400 mg/day), oxcarbazepine (at a dose between about 1200 mg and 2400 mg/day), pregabalin (at a dose between about 150 mg and 600 mg/day), tiagabine (at a dose between about 32 mg and 56 mg/day), topiramate (at a dose between about 200 mg and 400 mg/day), and valproate (at a dose between about 1200 mg and 1500 mg). Exemplary alpha-1-adrenergic receptor antagonists include, but are not limited to, prazosin administered at a dose of between about 0.5 mg to 15 mg/day.

In a further aspect, the invention is a pharmaceutical composition. The pharmaceutical composition comprises a therapeutically effective amount of cyclobenzaprine in combination with a drug selected from the group consisting of an alpha-1-adrenergic receptor antagonist, a beta-adrenergic antagonist, and an anticonvulsant. Generally, the amount of cyclobenzaprine in the pharmaceutical composition is between 0.1 mg to about 50 mg, between 0.5 to about 30 mg, or between 1 mg and 20 mg. Higher or lower doses are also contemplated. In one particular embodiment the amount of cyclobenzaprine is low to minimize side effects observed with higher amounts. The very low amounts are of less than 10 mg, less than 7 mg or less than 5 mg or less than 2.5 mg per day. Even lower amounts are also contemplated. In another embodiment of the invention, cyclobenzaprine is combined with a drug which may further alleviate the symptoms of fibromyalgia, multiple sclerosis, traumatic brain injury, Fabry's disease or Parkinson's disease. The drugs include an alpha-1-adrenergic receptor antagonist, a beta-adrenergic antagonist, an anticonvulsant, a selective serotonin reuptake inhibitor or a serotonin-norepinephrine reuptake inhibitor. Exemplary anticonvulsants include, but are not limited to carbamazepine (400 mg to 1200 mg), gabapentin (900 mg to 1800 mg), lamotrigine (100 mg to 400 mg), oxcarbazepine (1200 mg to 2400 mg), pregabalin (150 mg to 600 mg), tiagabine (32 mg to 56 mg), topiramate (200 mg to 400 mg), and valproate (1200 mg to 1500 mg). An exemplary alpha-1-adrenergic receptor antagonists includes, but is not limited to, prazosin in the amount of 0.5 mg to 15 mg. An exemplary selective serotonin reuptake inhibitor is escitalopram (in the amount of 10 mg and 20 mg).

Any suitable route of administration may be employed for providing the patient with an effective dosage of cyclobenzaprine. For example, buccal, oral, rectal, parenteral, transdermal, subcutaneous, sublingual, intranasal, intramuscular, intrathecal and the like may be employed as appropriate. The term parenteral as used herein includes subcutaneous, intracutaneous, intravenous, intramuscular, intra-articular, intrasynovial, intrasternal, intrathecal, intralesional and intracranial injection or infusion techniques. Dosage forms include tablets, such as scored tablets, coated tablets, or orally dissolving tablets; thin films, caplets, capsules (e.g. hard gelatin capsules), troches, dragees, dispersions, suspensions, solutions, patches and the like, including sustained release formulations well known in the art. In one preferred embodiment, the dosage form is an orally dissolving tablet or a thin film.

By "pharmaceutically acceptable carrier" is meant any diluent or excipient that is compatible with the other ingredients of the formulation, and which is not deleterious to the recipient. The pharmaceutically acceptable carrier can be selected on the basis of the desired route of administration, in accordance with standard pharmaceutical practices. Pharmaceutical compositions of the invention for parenteral administration can take the form of an aqueous or nonaqueous solution, dispersion, suspension or emulsion. In preparing pharmaceutical compositions of the invention for parenteral administration, cyclobenzaprine can be mixed with a suitable pharmaceutically acceptable carrier such as water, oil (particularly a vegetable oil), ethanol, saline solutions (e.g., normal saline), aqueous dextrose (glucose) and related sugar solutions, glycerol, or glycols such as propylene glycol or polyethylene glycol. Pharmaceutical compositions of the invention for parenteral administration preferably contain a water-soluble salt of cyclobenzaprine. Stabilizing agents, antioxidizing agents and preservatives can also be added to the pharmaceutical compositions for parenteral administration. Suitable antioxidizing agents include sulfite, ascorbic acid, citric acid and its salts, and sodium EDTA. Suitable preservatives include benzalkonium chloride, methyl- or propyl-paraben, and chlorbutanol.

In preparing pharmaceutical compositions of the invention for oral administration, cyclobenzaprine can be combined with one or more solid or liquid inactive ingredients to form tablets, capsules, pills, powders, granules or other suitable oral dosage forms. For example, cyclobenzaprine can be combined with at least one pharmaceutically acceptable carrier such as a solvent, filler, binder, humectant, disintegrating agent, solution retarder, absorption accelerator, wetting agent absorbent or lubricating agent. In one embodiment, cyclobenzaprine is combined with carboxymethylcellulose calcium, magnesium stearate, mannitol or starch, and is formed into tablets by conventional tableting methods.

Pharmaceutical compositions of the invention can be formulated so as to provide lymphatic absorption including pre-micellar and micellar mixtures to provide faster absorption in the small-intestine than the immediate release tablets or capsules through oral/GI route and to reduce or potentially bypass first-pass hepatic metabolism of cyclobenzaprine, for example by cytochrome P-450 3A4 as a CYP3A substrate, demethylation to norcyclobenzaprine (also known as desmethylcyclobenzaprine), or by glucuronidation (such as to cyclobenzaprine-N+-glucuronidate). Preferably, a controlled-release pharmaceutical composition of the invention is capable of releasing cyclobenzaprine into a subject at a rapid onset, so as to maintain a substantially constant or desired pharmacological activity for a given period of time, reduce or remove the effect of food on absorption, and to provide elimination of the drug and metabolites from the body with a reduced terminal elimination phase.

Pharmaceutical compositions of the invention can be formulated so as to provide buccal absorption including thin film formulations and orally dissolving tablets to provide faster absorption than the oral/GI route and to reduce or potentially bypass first-pass hepatic metabolism of cyclobenzaprine, for example by cytochrome P-450 3A4 as a CYP3A substrate, demethylation to norcyclobenzaprine (also known as desmethylcyclobenzaprine), or by glucuronidation (such as to cyclobenzaprine-N+-glucuronidate). Preferably, a controlled-release pharmaceutical composition of the invention is capable of releasing cyclobenzaprine into a subject at a rapid onset, so as to maintain a substantially constant or desired pharmacological activity for a given period of time, reduce or remove the effect of food on absorption, and to provide elimination of the drug and metabolites from the body with a reduced terminal elimination phase.

Pharmaceutical compositions of the invention can also be formulated so as to provide controlled-release of cyclobenzaprine upon administration of the composition to a subject, Preferably, a controlled-release pharmaceutical composition of the invention is capable of releasing cyclobenzaprine into a subject at a desired rate, so as to maintain a substantially constant or desired pharmacological activity for a given period of time. As used herein, a "controlled-release component" is a compound such as a lipid or mixture of lipids, liposome and/or microsphere that induces the controlled-release of cyclobenzaprine into the subject upon exposure to a certain physiological compound or condition. For example, the controlled-release component can be biodegradable, activated by exposure to a certain pH or temperature, by exposure to an aqueous environment, or by exposure to enzymes.

Formulation of controlled-release pharmaceutical compositions of the invention is within the skill in the art. Controlled release formulations suitable for use in the present invention are described in, for example, U.S. Pat. No. 5,674,533 (liquid dosage forms), U.S. Pat. No. 5,591,767 (liquid reservoir transdermal patch), U.S. Pat. No. 5,120,548 (device comprising swellable polymers), U.S. Pat. No. 5,073,543 (ganglioside-liposome vehicle), U.S. Pat. No. 5,639,476 (stable solid formulation coated with a hydrophobic acrylic polymer), the entire disclosures of which are herein incorporated by reference.

Biodegradable microparticles can also be used to formulate controlled-release pharmaceutical compositions suitable for use in the present invention, for example as described in U.S. Pat. Nos. 5,354,566 and 5,733,566, the entire disclosures of which are herein incorporated by reference.

In one embodiment, controlled-release pharmaceutical compositions of the invention comprise cyclobenzaprine and a controlled-release component. As used herein, a "controlled-release component" is a compound such as a polymer, polymer matrix, gel, permeable membrane, liposome and/or microsphere that induces the controlled-release of cyclobenzaprine into the subject upon exposure to a certain physiological compound or condition. For example, the controlled-release component can be biodegradable, activated by exposure to a certain pH or temperature, by exposure to an aqueous environment, or by exposure to enzymes. An example of a controlled-release component which is activated by exposure to a certain temperature is a sol-gel. In this embodiment, cyclobenzaprine is incorporated into a sol-gel matrix that is a solid at room temperature. This sol-gel matrix is implanted into a subject having a body temperature high enough to induce gel formation of the sol-gel matrix, thereby releasing the active ingredient into the subject.

In one embodiment, pharmaceutical compositions of the invention may comprise cyclobenzaprine and components that form micelles. Micelles containing cyclobenzaprine in the stomach and proximal small intestine facilitate absorption. Example of a micelle-component which is activated by exposure to a certain temperature is found in U.S. Pat. Nos. 6,761,903; 6,720,001; 6,383.471; 6,309,663; 6,267,985; and 6,248,363, incorporated herein by reference. In this embodiment, cyclobenzaprine is incorporated into a soft-gel capsule, Such components may mimic the augmentation of absorption termed the "food effect", and such formulations may provide more predictable absorption by eliminating the "food effect" from dietary sources.

The composition of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The magnitude of a prophylactic or therapeutic dose of the active ingredient (i.e., cyclobenzaprine metabolite thereof) in the prevention or treatment of a human will vary with the type of affliction, the severity of the patient's affliction and the route of administration. The dose and dose frequency will also vary according to the age, weight and response of the individual patient. In a preferred embodiment, one dose is given at bed time or up to several hours before bedtime to facilitate the achievement of deep, refreshing sleep. Bedtime may be any hour of the clay at which a person engages in the most extensive period of sleep.

In order that this invention to be more fully understood, the following examples are set forth. These examples are for the purpose of illustration only and are not to be construed as limiting the scope of the invention in any way. The practice of the invention is illustrated by the following non-limiting examples.

EXAMPLES

Example 1

Tablet Formulation

A typical oral formulation for coated tablets consists of the following:
Formula quantity per tablet (mg.) cyclobenzaprine 1.0, lactose 74.0, corn starch 35.0, water (per thousand tablets) 30.0 ml, magnesium stearate 1.0, corn starch 25.0 The active ingredient (cyclobenzaprine) is blended with the lactose until a uniform blend is formed. The smaller quantity of corn starch is blended with a suitable quantity of water to form a corn starch paste. This is then mixed with the uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration.

Tablets are coated by standard aqueous or nonaqueous techniques. For example, 2.5 mg of hydroxypropymethylcellulose can be dissolved in 25 mg of deionized water. An aqueous (10 mg) suspension of 1.88 mg talc, 0.5 mg of titanium dioxide, 0.1 mg of yellow iron oxide, and 0.02 mg of red iron oxide is stirred into this solution. The coating suspension is sprayed on the tablets and the coated tablets are dried overnight at 45° C.

Example 2

Development of an Optimized Gelcap Formulation of VLD Cyclo for Fatigue

We are developing a novel gelcap that employs a specific mixture of lipids to form micelles containing cyclobenzaprine that is expected to speed upper GI absorption, increase efficiency of absorption (in stomach and proximal small intestine); decrease or eliminate food effect (which is 20% for the Amrix formulation of cyclobenzaprine) and speed elimination (since lower absorption may prolong the terminal elimination phase in existing formulations). The gelcap formulation is expected to result in increased dosage precision; decreased potential for morning "hangover"; and potentially more rapid induction of sleep.

The lipid formulation is designed to form micelles in gastric-intestinal fluids, to solubilize cyclobenzaprine in the stomach and small intestine and to increase the rate, efficiency and predictability of absorption of cyclobenzaprine in the bloodstream. Cyclobenzaprine assumes a positive charge in the acidic gastric fluid. Micelles and charged cyclobenzaprine are highly soluble in gastric fluid. In the small intestine, the pH increases and cyclobenzaprine starts to lose its charge. Uncharged cyclobenzaprine molecules have poor solubility without micelles. The micelles prevent precipitation of the uncharged cyclobenzaprine by solubilizing it in their cores and to deliver the cyclobenzaprine to the wall of the small intestine where the cyclobenzaprine can be absorbed into the bloodstream. The lipid formulation is referred to as pro-micellar because prior to interacting with aqueous fluid, the lipids do not form micelles. The pro-micellar mixtures are typically encased in a gelatin capsule (gelcap).

Example 3

Cyclic Alternating Pattern Analysis

VLD CBP Effects on CAP A2+CAP A3

Subsequent to enrollment and completion, EEG sleep studies in FM patients were reported that identified increases in the periodic sleep EEG arousal disorder known as the cyclic alternating pattern (CAP) in non-REM sleep. (Rizzi et al. J. Rheumatol. 2004, (6):1193-1199, Rosa et al. 1999, 110(4):585-592). Therefore, an analysis of sleep EEG CAP was performed that measured subtypes CAP A1, CAP A2, and CAP A3 and Total CAP (or CAP A1+A2+A3). Subtype CAP A1 is associated with sleep maintenance or least sleep instability, and subtypes CAP A2 and A3 are associated with moderate to prominent increases in sleep instability.

Because CAP A2 and A3 are most closely associated with sleep instability[26,27], the sum of $CAP_{A2}+CAP_{A3}$ rates ($CAP_{A2+A3}$) was used as an indicator of disordered sleep. $CAP_{A2+A3}$ was normalized ($CAP_{A2+A3(Norm)}$) by dividing $CAP_{A2+A3}$ by the total CAP rate ($CAP_{total}=CAP_{A1}+CAP_{A2}+CAP_{A3}$ rates=$CAP_{A1+A2+A3}$) and expressed as a percentage. Therefore, $CAP_{A2+A3(Norm)}=100*CAP_{A2+A3}/CAP_{A1+A2+A3}$ and this reflects the percentage of total CAP that is associated with sleep instability.

To determine whether patients experienced nights with a potential CAP response to treatment, it was necessary to determine an empirical threshold below which $CAP_{A2+A3(Norm)}$ values reflect a night of relatively stable sleep for this population. To determine a threshold for $CAP_{A2+A3(Norm)}$ that could be informative for a potential treatment response, the study CAP data were then evaluated by considering a range of cutoff values for $CAP_{A2+A3(Norm)}$ from 1.0% to 50%. Testing various $nCAP_{A2+A3}$ values revealed that defining a threshold for response $CAP_{A2+A3(Norm)} \leq 33\%$ distinguished WAD CBP-treated subjects from placebo-treated subjects at which threshold, the percentage of patients with increased nights of CAP response while on treatment (ITT, LOCF) was 72% with VLD CBP vs. 33% with placebo (p=0.019).

Correlation of $CAP_{A2+A3(Norm)}$ with FM Symptoms.

To evaluate whether increased nights with $CAP_{A2+A3(Norm)} \leq 33\%$ was correlated with clinical improvement measures in pain, fatigue, tenderness, HAD, and HAD depression, over the course of the study (LOCF week 8), Spearman's rank correlation was then investigated separately for each treatment. Data were coded such that improvements were positive. Within the VLD CBP treated patients, increased nights with $CAP_{A2+A3(Norm)} \leq 33\%$ was correlated positively to decreases in fatigue (rho=0.62, p=0.006), HAD total score (rho=0.505, p=0.033), HAD depression subscale (rho=0.556, p=0.017), patient-rated fatigue (rho=0.614, p=0.007) and clinician-rated fatigue (rho=0.582, p=0.0112). In contrast, improved CAP response was not correlated with either musculoskeletal pain or dolorimetry. Within the Placebo-treated subjects, none of these FM symptoms or Sleep EEG parameters was significantly correlated to increased number of nights with $CAP_{A2+A3(Norm)} \leq 33\%$. In the placebo group, increased nights of CAP response correlated with measures of improved sleep: a positive correlation with sleep efficiency and a negative correlation with total time awake. Together, these findings show that nights with $CAP_{A2+A3(Norm)} \leq 33\%$ reflect relatively healthy or restorative sleep for FM patients as symptoms vary naturally over the course of the condition, as well as providing a potential biomarker for treatment effects of low dose cyclobenzaprine for disordered sleep.

Example 4

Treatment of Multiple Sclerosis

A 46 year old woman was diagnosed with multiple sclerosis three years ago. Her last flare-up was treated with a short course of steroids, and she has been symptom free for two months. However, she has noted that throughout the day she has very low energy levels. Her capacity for physical and mental work has declined to the point where she is unable to function at work. She reports getting 6 to 8 hours of sleep each night but feels unrefreshed in the morning. Taking naps or getting more sleep does nothing to improve her energy level. She began taking cyclobenzaprine initially at a dose of 2 mg at bedtime. Her doctor increased the dose to 4 mg at bedtime. With each does she felt that the quality of her sleep improved and her level of energy increased during the day. Within three weeks, her physical stamina as well as her ability to concentrate and focus increased to the extent that she was able to resume occupational functioning. Her doctor asks her to assess her level of fatigue on a scale oft to 10 before and after cyclobenzaprine treatment. Before treatment she assessed herself as having 9/10 fatigue. After treatment her level of fatigue decreased to 3/10.

Example 5

Treatment of Traumatic Brain Injury

A 27-year-old male survived a serious motor vehicle accident with closed head trauma. He underwent six months of physical rehabilitation. However, he was left with mild spasticity and hyper-reflexia of the upper extremities, general cognitive slowing, and mild language difficulties. Other symptoms including pronounced emotional lability often manifested as outbursts of anger or uncontrollable crying spells. These symptoms were felt by his neurologist to be consistent with traumatic brain injury. Because of the spasticity, the neurologist recommended six months of additional physical rehabilitation. However, the patient was unable to make progress with his physical rehabilitation because his physical energy level and motivation would drop very rapidly during the course of his rehabilitation sessions. He was unable to complete many of the exercises or follow complex instructions. If sleep is poor or, characterized by both difficulty falling asleep and early-morning awakening. His neurologist prescribed cyclobenzaprine at a dose of 5 mg at bedtime. Within three weeks, the patient's sleep improved substantially and his level of energy and concentration were markedly better. He was able to complete rehabilitation and make significant gains in physical capacity.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

We claim:

1. A method for monitoring the effectiveness of cyclobenzaprine treatment for disordered sleep in a subject at risk of suffering from disordered sleep, who has received the cyclobenzaprine treatment, the method comprising:

a) measuring the CAP A1, A2 and A3 rates in the subject;
b) generating an nCAP A2+A3 ($CAP_{A2+A3(Norm)}$) value from the measurements in a); and
c) monitoring the effectiveness of the cyclobenzaprine treatment for disordered sleep wherein the cyclobenzaprine treatment is effective when the $CAP_{A2+A3(Norm)}$ value generated in step b) is less than or equal to a threshold $CAP_{A2+A3(Norm)}$ value generated in subjects suffering from disordered sleep who have received a placebo.

2. The method of claim 1, wherein the specified $CAP_{A2+A3(Norm)}$ threshold value is ≤33%.

* * * * *